United States Patent
Xia et al.

(10) Patent No.: US 11,428,440 B2
(45) Date of Patent: Aug. 30, 2022

(54) METHOD FOR MAKING PORPHYRIN COVALENT ORGANIC FRAMEWORK-BASED INTERFACE

(71) Applicant: UCHICAGO ARGONNE, LLC, Chicago, IL (US)

(72) Inventors: Zijing Xia, Chicago, IL (US); Hao-Cheng Yang, Westmont, IL (US); Zhaowei Chen, Downers Grove, IL (US); Seth B. Darling, Chicago, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 16/407,841

(22) Filed: May 9, 2019

(65) Prior Publication Data

US 2020/0355403 A1    Nov. 12, 2020

(51) Int. Cl.
| | | |
|---|---|---|
| *C07D 487/22* | (2006.01) | |
| *C09K 5/14* | (2006.01) | |
| *F24S 70/10* | (2018.01) | |
| *F24S 70/65* | (2018.01) | |
| *F24S 80/00* | (2018.01) | |

(52) U.S. Cl.
CPC .......... *F24S 70/10* (2018.05); *C07D 487/22* (2013.01); *C09K 5/14* (2013.01); *F24S 70/65* (2018.05); *F24S 2080/011* (2018.05); *F24S 2080/013* (2018.05); *F24S 2080/017* (2018.05)

(58) Field of Classification Search
CPC ...... F24S 70/10; F24S 70/65; F24S 2080/013; F24S 2080/017; F24S 2080/011; C07D 487/22; C09K 5/14
See application file for complete search history.

(56) References Cited

U.S. PATENT DOCUMENTS

2004/0202876 A1*  10/2004  Kobuke ............... H01G 9/2059
                                                          428/457

FOREIGN PATENT DOCUMENTS

| CN | 103951801 A | * | 7/2014 | |
| CN | 107641185 A | * | 1/2018 | ............. C08G 12/26 |
| CN | 108219160 A | * | 6/2018 | ............. C08G 12/26 |

OTHER PUBLICATIONS

Xia, Z.-J.; Yang, H.-C.; Chen, Z.; Waldman, R. Z.; Zhao, Y.; Zhang, C.; Patel, S. N.; Darling, S. B. Porphyrin Covalent Organic Framework (POF)-Based Interface for Solar Steam Generation. Advanced Materials Interfaces 2019, 6, 1900254 (Year: 2019).*
Shang & Deng, "Solar steam generation: Steam by thermal concentration," Nature Energy 1, 16133, 2 pages (2016).
Gao, et al., "Solar absorber material and system designs for photothermal water vaporization towards clean water and energy production," Energy & Environmental Science, 24 pages (2018).

(Continued)

*Primary Examiner* — William P Fletcher, III
(74) *Attorney, Agent, or Firm* — Foley & Lardner LLP (57) ABSTRACT

A porphyrine organic framework ("POF") material is introduced with a one-pot method for photothermal material fabrication. The POF material may be deposited on a support scaffold by reacting a pyrrole by acid-catalyzed dehydration forming a plurality of porphyrin-based covalent organic frameworks particles on the support scaffold.

11 Claims, 10 Drawing Sheets

(56) References Cited

OTHER PUBLICATIONS

Li, et al., "MXene Ti3C2: An Effective 2D Light-to-Heat Conversion Material," ACS Nano 11(4), pp. 3752-3759 (2017).
Li, et al., "A porphyrin covalent organic framework cathode for flexible Zn-air batteries," Energy & Environmental Science 11(7), pp. 1723-1729 (2018).
Wang, et al., "Self-Floating Carbon Nanotube Membrane on Macroporous Silica Substrate for Highly Efficient Solar-Driven Interfacial Water Evaporation," ACS Sustainable Chemistry & Engineering 4(3), pp. 1223-1230 (2016).
Wang, et al., "High-Performance Photothermal Conversion of Narrow-Bandgap Ti2O3 Nanoparticles," Advanced Materials 29(3), 1603730, 6 pages (2017).
Xu, et al., "Mushrooms as Efficient Solar Steam-Generation Devices," Advanced Materials 29(28), 1606762, 5 pages (2017).
Zhang, et al., "Hydrophobic Light-to-Heat Conversion Membranes with Self-Healing Ability for Interfacial Solar Heating," Advanced Materials 27(33), pp. 4889-4894 (2015).
Zhou, et al., "Self-assembly of highly efficient, broadband plasmonic absorbers for solar steam generation," Science Advances 2(4), e1501227, 8 pages (2016).

\* cited by examiner

METHOD FOR MAKING PORPHYRIN COVALENT ORGANIC FRAMEWORK-BASED INTERFACE

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to photothermal materials, more specifically to porphyrin covalent organic framework ("POF") based interfaces for steam generation.

BACKGROUND

Water and energy represent two essential—and intertwined—elements of life and society. With expanding population and global development, both freshwater and energy supplies are increasingly strained. Purification of water is energy-intensive, but state-of-the-art technologies (viz., reverse osmosis) are already close to the thermodynamic limit on energy efficiency. In order to continue reducing the cost of water purification, one must reduce the cost of the energy itself by resorting to abundant renewable sources.

Existing methods to mitigate clean water shortages at the expense of greater energy resource exploitation are not a sustainable solution. Further, newer concerns regarding water usage and contamination continue to arise, such as residuals management in the oil and gas industry, most notably the increasing need to address contaminated fracking water.

Solar-driven water evaporation for treatment of seawater or wastewater is one promising strategy to help address this challenge because it draws on plentiful sunlight as the clean renewable source. For solar steam generation to be effective, one needs evaporators that can float to concentrate heat energy at the water-air interface, where evaporation takes place. Ideally, though, high-performance solar steam generators must also have the following characteristics: (1) being buoyant on water; (2) absorbing a broad spectrum of light effectively in order to utilize most of the energy from solar irradiation; (3) converting light to heat efficiently; (4) having a porous structure to efficiently transfer heat to the water and to provide for transport pathways from the bulk to the surface; and (5) having low thermal conductivity to minimize heat losses to the underlying water body.

Various solar absorber (photothermal) materials have been reported for photothermal water evaporation. Conventional absorber materials can be categorized into carbon materials, plasmonic metals, semiconducting materials, and advanced materials, such as polymers and Mxene. Of those, carbon materials show the significant advantages of ultra-high solar absorbance, good stability, low cost, and abundance. Well-known carbon materials, such as graphene and carbon nanotubes, have been fabricated into films, foams, or sponges and then applied in solar steam generation, but the economic scalability for these materials is unclear, particularly for wide-scale use or adoption in remote or resource-poor locations.

However, most of these materials cannot fulfill the sundry requirements listed above. Therefore, assistant materials are often employed in solar steam generator design, and it has become popular to fabricate multilayer-structured generators combining an absorbing layer and an assisting layer. The synthesis processes used to prepare these materials are often complex, which can limit scalability and reduce efficiency.

Covalent organic frameworks ("COFs") are a class of advanced porous materials with abundant diversity in structure and composition. COFs were first reported in 2005 by Yaghi and coworkers. Since then, COFs have been applied in research areas such as carbon capture, gas storage, gas separation, and catalysis. To date, COFs have not been explored as photothermal materials. In designing a COF for such an application, one aims to incorporate specific properties of the constituent molecular species. Porphyrins are conjugated and highly delocalized organic molecules with a strong ability to coordinate metal cations into complexes. These characteristics make porphyrin and porphyrin-derived structures promising candidates for solar steam generation and multifunctional application in water-energy systems. Li and coworkers recently reported a mild synthesis method to obtain porphyrin-based covalent organic frameworks (POFs). See, e.g., B. Li, S. Zhang, B. Wang, Z. Xia, C. Tang, Q. Zhang. Energy Environ. Sci. 2018, 11, 1723-1729 and L. Kong, B. Li, H. Peng, R. Zhang, J. Xie, J. Huang, Q. Zhang. Adv. Energy Mater. 2018, 8, 1800849.

SUMMARY

Embodiments described herein relate generally to photothermal material. The material comprises a porous support scaffold and a plurality of porphyrin-based covalent organic frameworks particles formed on the porous support scaffold.

Some embodiments relate to a method of fabricating a photothermal material comprising providing a support scaffold and reacting a pyrrole by acid-catalyzed dehydration forming a plurality of porphyrin-based covalent organic frameworks particles on the support scaffold.

In some embodiments, a method of forming a POF material is described. A precursor solution is formed by weak acid to provide an acidic environment, such as 100 mL acetic acid, added to a reaction vessel. An acid catalyst, such as 50 μL of trifluoroacetic acid ("TFA"), is added to the reaction vessel. Pyrrole is added to the reaction vessel, such as about 20 μL (for example, 22.7 μL) pyrrole, and about 20 mg (for example, 23.44 mg) terepthalaldehyde in about 300 μL nitrobenzene solvent. In one embodiment, the pyrrole is present in a nitrobenzene solvent prior to mixing with the terepthalaldehyde. The pyrrole and terepthalaldehyde react via acid-catalyzed dehydration to form a POF material on a support framework.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIGS. 2A-2L illustrate the uncoated, coated, and infrared images for samples.

FIGS. 3A-3H are SEM images of AAO membrane, wood, sponge, and fiber before and after in situ growth of POF. FIGS. 3E-3H are AAO@POF, wood@POF, sponge@POF, and fiber@POF, respectively.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Figure 1A:
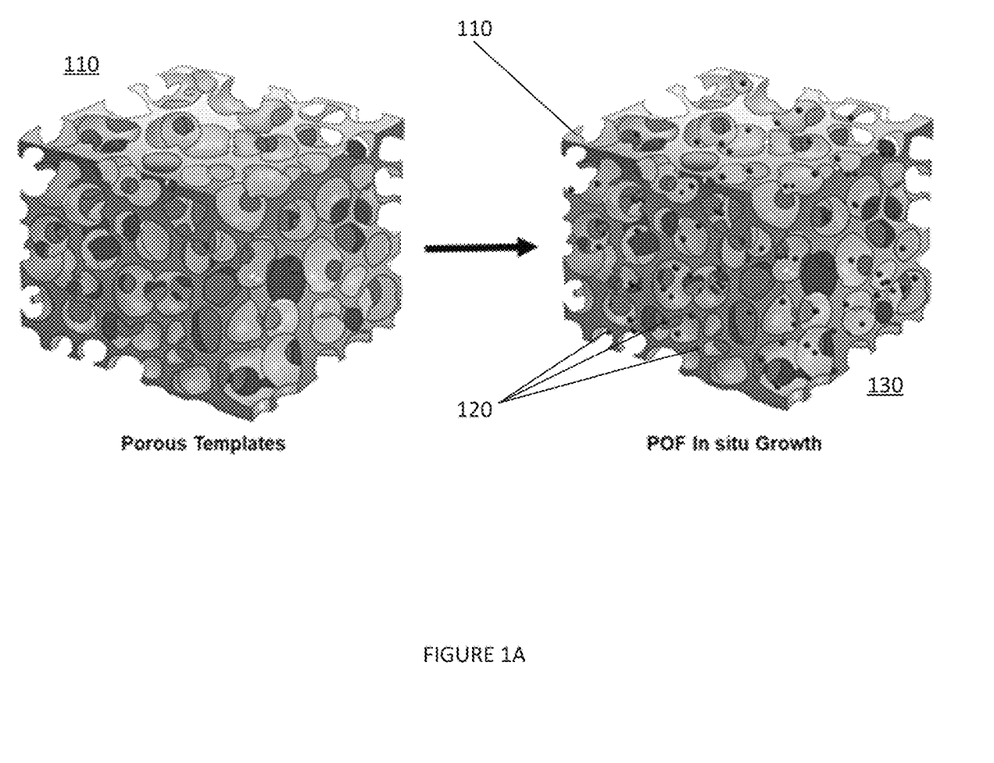
FIG. 1A shows a schematic for one embodiment of a synthesis process for POF-based solar steam generator.
Figure 1B:
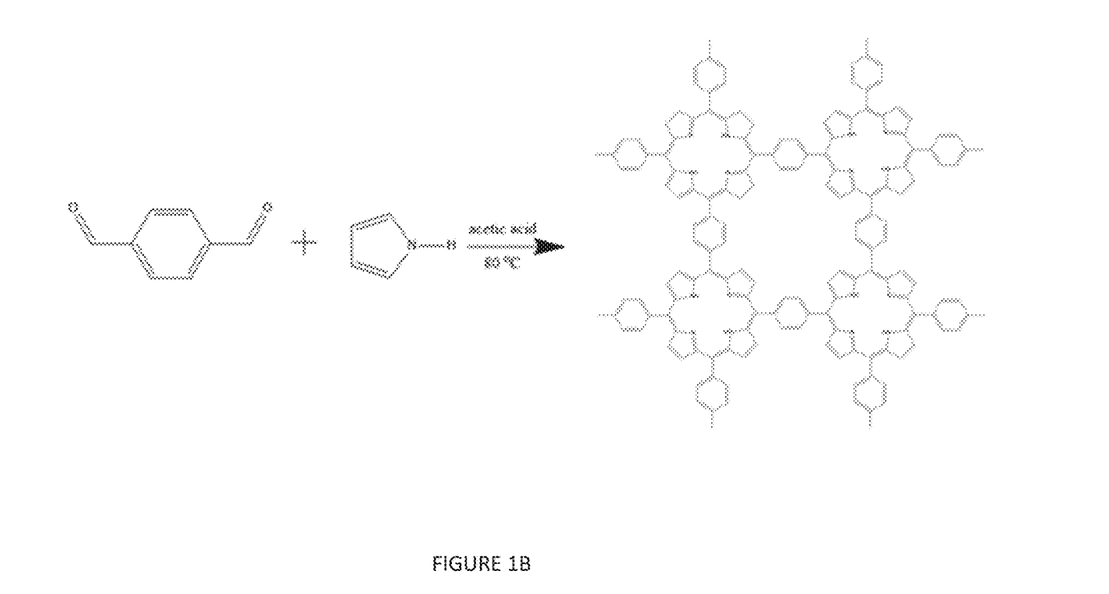
FIG. 1B shows one embodiment of a direct synthesis of POF of FIG. 1A.

A POF material is introduced with a one-pot method for photothermal material fabrication. Embodiments described herein relate generally to POFs as photothermal materials for solar steam generation. In one embodiment, the process is a single-step, one-pot method, suggesting it could be readily scaled up at low cost. There is enormous flexibility regarding the materials used as the supporting scaffold for these POFs, enabling one to select an available material to meet local needs. The template POF materials were one-pot synthesized following an acid-catalyzed dehydration reaction with benzene-1,4-dialdehyde ("BDA") and pyrrole as the substrates and porous structured materials as templates. Pure POF exhibits a dense spherical morphology with a diameter of about 1.0 µm (see FIG. 6). FIG. 1A depicts the scheme for in situ growth of POFs within porous templates. The POF-based materials showed strong performance in sunlight-driven water evaporation. Wood POF was particularly effective, presenting high evaporation efficiency (~84%). FIG. 1B illustrates a particular embodiment of POF utilized herein as an example. The synthesis and characterization of this POF is described in, for example, B. Li, S. Zhang, B. Wang, Z. Xia, C. Tang, Q. Zhang, Energy Environ. Sci. 2018, 11, 1723-1729 and L. Kong, B. Li, H. Peng, R. Zhang, J. Xie, J. Huang, Q. Zhang, Adv. Energy Mater. 2018, 8, 1800849, both incorporated herein by reference.

The process includes the selection of a support scaffold 110 to serve as a growth template and structural support for the POF particles 120. The support scaffold 110 is selected while taking into consideration surface area, hydrophilicity, and density. Those of skill in the art will appreciate that the intended end use of the material will determine the appropriate support scaffold materials and properties, limited by the compatibility of the support scaffold. The support scaffold 110 should include nucleation sites for POF particles 120 to grow in situ on the surfaces of support scaffold 110. In some embodiments, the support scaffold 110 is a porous material. For example, in one embodiment, the pores may be at least 10 nm or about 10 nm in average diameter (i.e., nanometer scale pores). In another embodiment, the pores may be at least 10 µm or about 10 µm in average diameter (i.e., micron scale pores). In another embodiment the pores may be at least 10 mm or about 10 mm in average diameter (i.e., millimeter scale pores). One of skill will appreciate that the solvent and reactants should be able to travel into the pore network, placing some restriction on the size of the pores. The pore size should consider water transport, heat transport, and light absorption, balancing those factors. Further, the roughness of the support scaffold is also considered in some embodiments. For example, reflectance can be further reduced (relative to smooth materials) by using materials with macroscopically rough structures such as sponge or wood. In one embodiment, the roughness is on the order of the wavelengths of the light to be scattered. In addition to pore size, support scaffold selection may also need to consider the thermal conductivity, density, and structure of templates.

Suitable support scaffolds include, but are not limited to: wood, AAO membrane, sponge, cork, ceramic, and fabric. Among these commonly available materials, wood is a nearly ideal option since it satisfies most of the requirements for solar steam generators. Wood possesses low thermal conductivity, high hydrophilicity, and a porous internal network comprised of microvoids and cell wall capillaries. In one embodiment, the material has a water contact angle of 90 degrees or less. In one embodiment, the material has a therma conductivity below 1 W/(m K).

With a support scaffold selected, the support scaffold is placed in a precursor solution. The precursor solution is formed by weak acid to provide an acidic environment, such as 100 mL acetic acid, added to a reaction vessel. An acid catalyst, such as 50 µL of TFA, is added to the reaction vessel. For example, in one embodiment pyrrole and tetraphthaladehyde are utilized to generate the repeating unit structure of porphyrin for the POF, added in about a 1:1 ratio in an acidic environment. Specifically, in one example, pyrrole is added to the reaction vessel, such as about 20 μL (for example, 22.72 μL) pyrrole, and about 20 mg (for example, 23.44 mg) terepthalaldehyde, and optionally about 300 μL nitrobenzene. In one embodiment, the general ratio is 20 μL pyrolle/20 mg terepthalaldehyde/300 μL nitrobenzene in an acidic environment of 100 ml acetic acid and 50 μL TFA for the respective materials. These ratios may be scaled (such as where x is 1-10). The contents of the reaction vessel may be mixed. In one embodiment, the support scaffold is included in the reaction vessel, allowing for "one-pot synthesis." In another embodiment, the precursor solution is formed and then added to the support scaffold.

The reaction to form the POF results in POF particles that are formed on the surfaces of the support scaffold. The POF particles preferably have an average diameter of 1 um.

In one embodiment, a layer of POF particles are grown. The layer may comprise, for example, a single particle thick layer. The layer may be discontinuous such that the discrete nanoparticle structure remains rather than forming a monolayer. From macroscale, all the materials are black all over the surface. In microscale, from SEM images (FIGS. 3E-3H), about 20-50% surface area coverage.

The support scaffold is subjected to POF in situ for a period of time, the reaction period being 3 hours to 72 hours and ranges, inclusive, such as 3-24 hours, 3-12 hours, or 6-12 hours. Temperature ranges for the POF in situ exposure and reaction are preferably 50-150° C., inclusive, such as 80-130° C. or about 80° C.

Following the formation of the POF particles on the support scaffold, the resultant material can be washed, such as by polar and nonpolar solvents, with or without agitation (e.g., sonication), to form a photothermal material. Temperature ranges for the drying are preferably 50-150° C., inclusive, such as about 100° C.

Optionally, the photothermal material may be dried to form a resultant POF photothermal material. Thermal drying may be utilized. The temperature during drying should be sufficiently low as to not damage the substrate or POF. Temperature ranges for the POF in situ exposure and reaction are preferably 50-150° C., inclusive, such as 80-100° C. or about 80° C. The drying may be until the material has reached a desired moisture content or for a set period such as for a period of time, the reaction period being 0.5-6 hours, inclusive, such as 1-4 hours.

Experiment.

Fabrication of Templates@POF.

The AAO and PVDF membranes were purchased from Sterlitech (USA) and MilliporeSigma (USA), respectively. The fabric, melamine sponges, and basswood were obtained from Fisher Scientific (USA). The terephthalaldehyde, pyrrole, TFA, nitrobenzene, and acetic acid were purchased from Sigma-Aldrich (USA). Templates@POF were synthesized using a one-pot method. An acid-catalyzed dehydration reaction leads to uniform in situ growth on a variety of different substrates. The selected substrate material (AAO membrane, fabric, sponge, or wood) is trimmed as needed to achieve the desired form factor and placed into the reactor. 100 mL acetic acid is added to the vessel, followed by addition of 50 μL TFA to serve as an acid catalyst. Next, 22.72 μL pyrrole, 300 μL nitrobenzene, and 23.44 mg terephthalaldehyde are mixed with the suspension. The as-obtained mixture was kept at 80° C. under continuous magnetic stirring for 24 hours and then cooled down to room temperature. The black products were washed using acetone, isopropyl alcohol, and deionized water twice. Ultrasonic cleaning for 30 minutes served to remove any weakly bonded POF particles. After drying in a vacuum oven at 100° C. for 2 hours, the black templates@POF were obtained for further characterization.

Characterization.

The particle size distribution was detected by a particle size analyzer (Zetasizer Nano, Malvern). The surface structures and morphologies of templates@POF and pristine templates were characterized using a JSM7500F (JEOL Ltd., Tokyo, Japan) field emission scanning electron microscope (FE-SEM) at 3.0 kV. The UV-Vis-NIR reflection and absorption spectra of templates@POF and POF solution were collected using an UV-Vis-NIR spectrometer (Lambda 950, PerkinElmer). The water evaporation tests were all conducted using a solar simulator (Oriel 300 W, Newport). The infrared images were taken with a FLIR C2 Compact Thermal Imaging Camera, and the temperature vs. time data were collected using an infrared gun.

Density Functional Theory.

The QUANTUM ESPRESSO package was applied. SG15 ONCV pseudopotential is used for all elements. The exchange-correlation part of the density functional was treated within the generalized gradient approximation ("GGA") of Perdew-Burke-Ernzerhof ("PBE"). The cut-off energy for the plane-wave basis was 50 Ry. The basic calculations were performed in the unit cell consisting of 54 atoms ($C_{32}N_4H_{18}$), with a k-point mesh of 5×5×1, and the total energy is converged to $1×10^{-4}$ eV.

Results and Discussion.

The coated materials were washed, sonicated, and dried, producing four types of optically black templates@POF (FIGS. 2A-2H). POFs successfully grew on the exterior and interior surfaces of all the tested template materials. Under simulated sunlight irradiation, all the templates@POF show excellent photothermal properties, with surface temperatures over 90° C. (FIGS. 2I-2L), which indicates that POF-based materials are promising candidates for solar steam generation.

Figure 6:
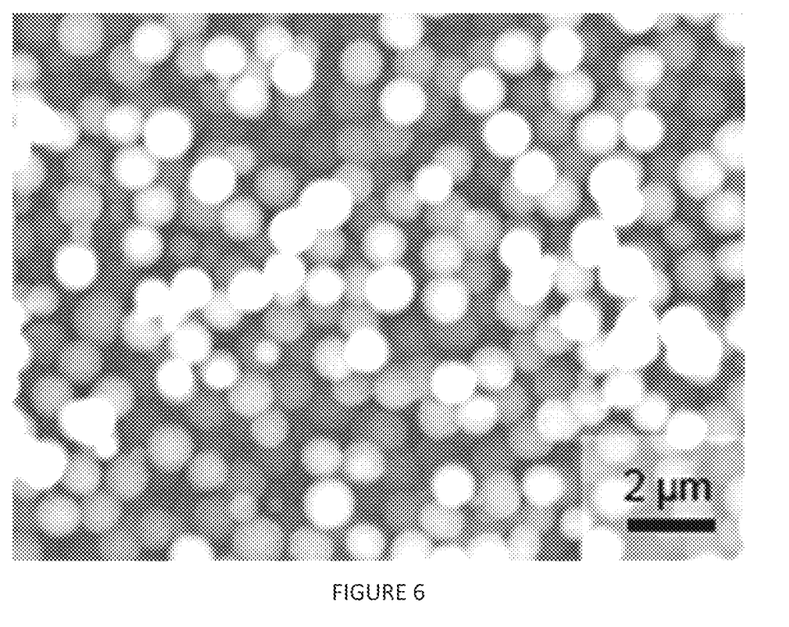
FIG. 6 is an SEM image of POF particles.
Figure 7:
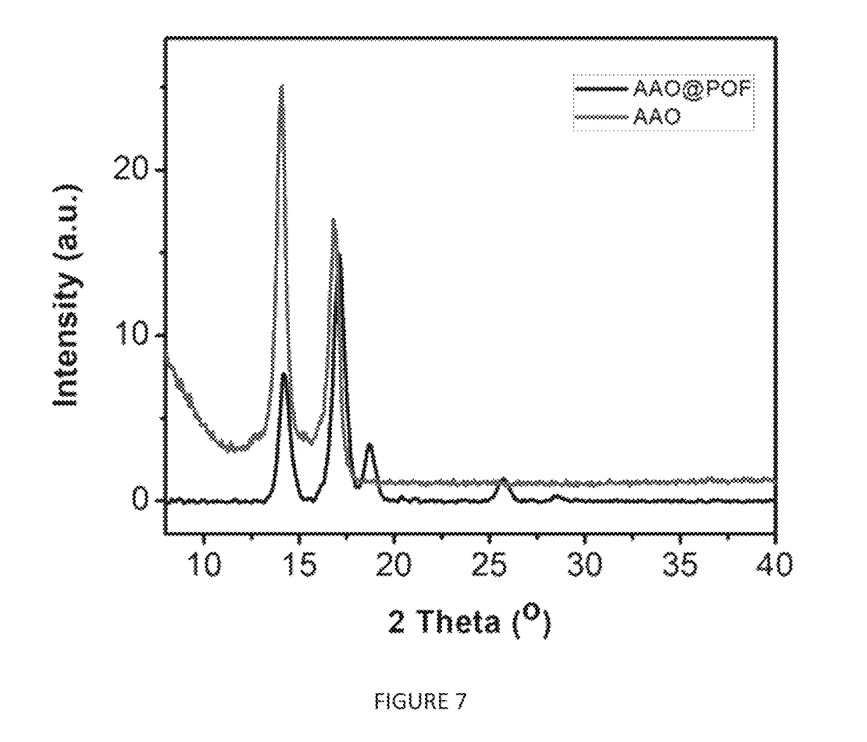
FIG. 7 is XRD spectrum of AAO membrane and AAO@POF wavelength dispersion.
Figure 8A:
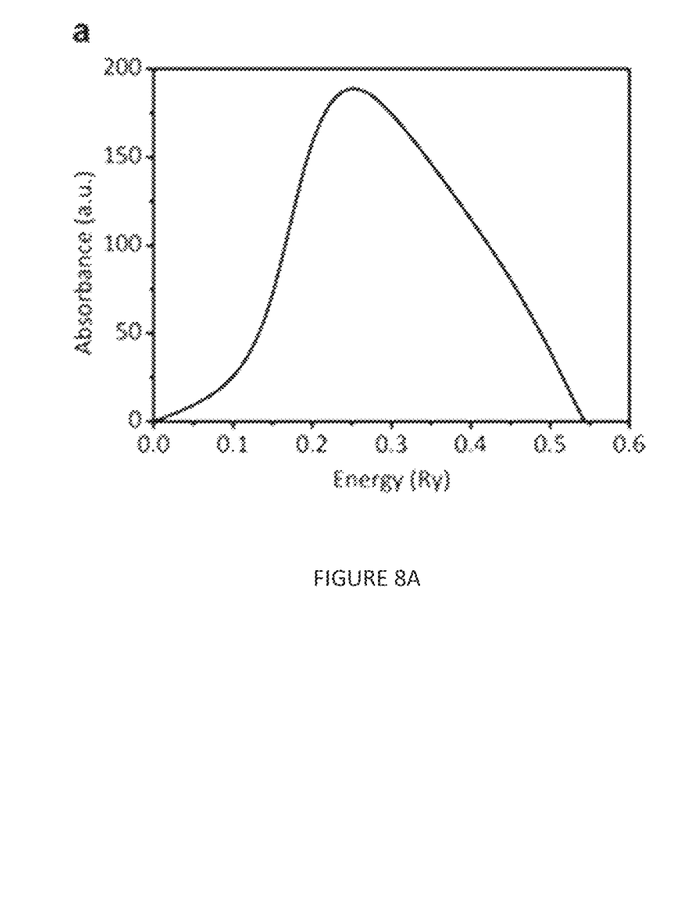
FIG. 8A is a graph of the PW DFT calculation result of POF light absorbance with energy dispersion.
Figure 8B:
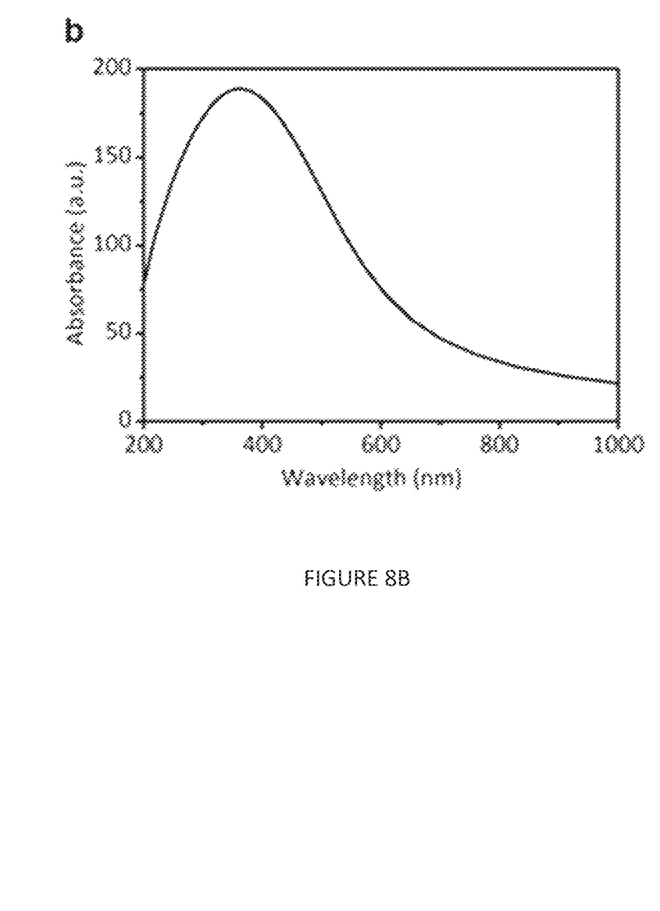
FIG. 8B is a graph of the PW DFT calculation result of POF light absorbance with wavelength dispersion.

The surface morphologies of templates@POF before and after in situ growth were observed by field-emission scanning electron microscope ("FESEM"). The nascent template materials exhibit porous or layered structures. POF particles were dispersed evenly on the surface of the templates. The size of the POF particles could be controlled easily by adjusting the reaction temperature and/or reaction time. In order to claim "tenability," it would be helpful to provide a roadmap in the application for how the POF particle properties can be adjusted. For example, increasing temperature within the ranges described increases the homogeneity of the pore size, with POF particles becoming relatively more monodispersed. In one embodiment, the average particle size is about 1000 nm at 80° C. Further, reaction time is associated with the average particle size. Longer reaction times, such as up to 72 hours, result in larger average particle sizes while shorter reaction times, such as down to 3 hours, result in smaller average particle sizes. For example, for a 24-hour reaction time, the particles may have an average diameter of 1000 nm. Further, one of skill in the art would understand temperature and reaction time to be interrelated and have a cumulative impact on the formation of the POF particles. In this study, all reactions were consistently maintained at 80° C. for 24 hours. The morphology of the scaffolds is unaffected by the synthesis process, other than the appearance of adhered POF particles. The structure of the surface-bound POF particles themselves is also the same as the POF grown in solution (FIG. 6). X-ray diffraction ("XRD") showed that the POFs possess a characteristic peak at 18.3° (FIG. 7).

Figure 2A:
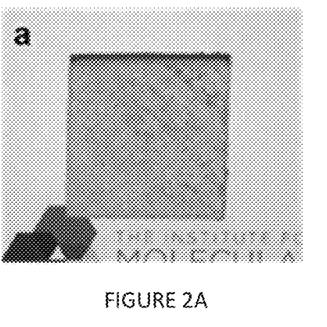
FIG. 2A is a digital picture of wood.
Figure 2B:
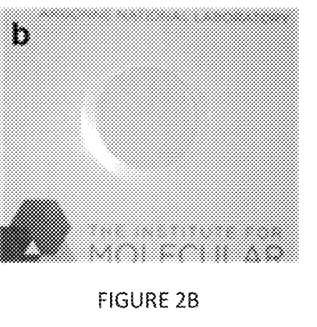
FIG. 2B is a digital picture of AAO membrane.
Figure 2C:
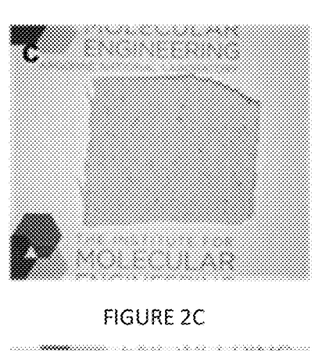
FIG. 2C is a digital picture of fabric.
Figure 2D:
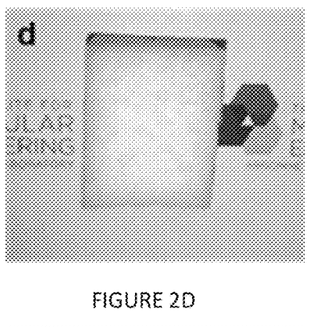
FIG. 2D is a digital picture of sponge.
Figure 2E:
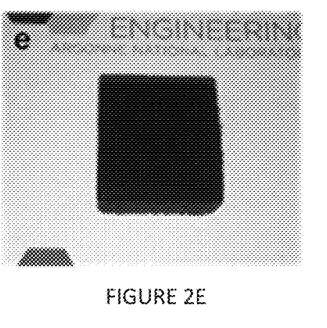
FIGS. 2E-2H illustrate the corresponding samples of FIGS. 2A-D after in situ POF growth.
Figure 2F:
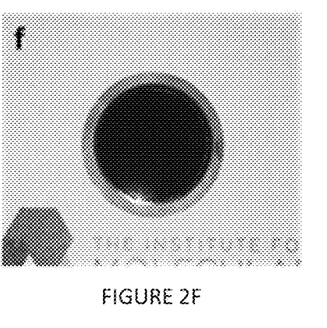
Figure 2G:
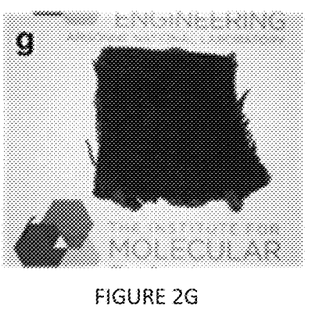
Figure 2H:
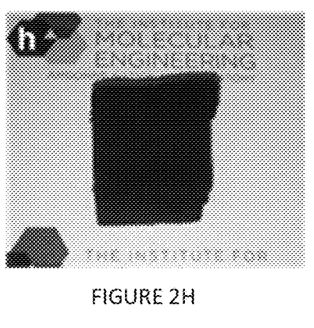
Figure 2I:
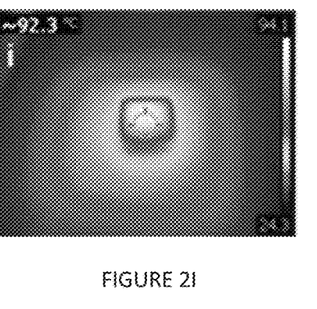
FIGS. 2I-2L illustrate infrared images of respective POF-based materials under simulated sunlight.
Figure 2J:
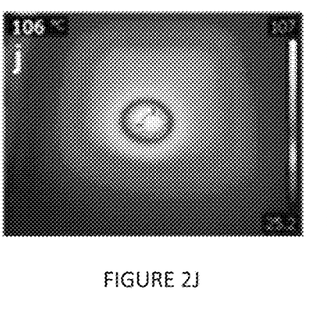
Figure 2K:
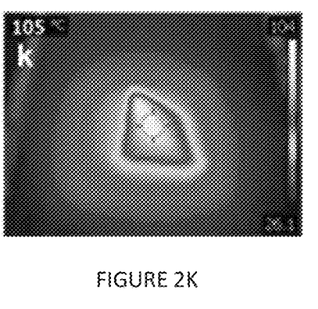
Figure 2L:
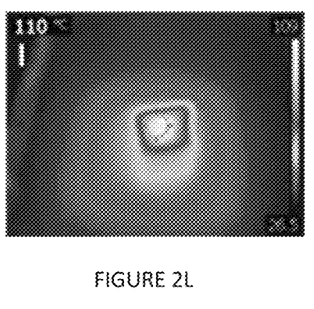
Figure 3A:
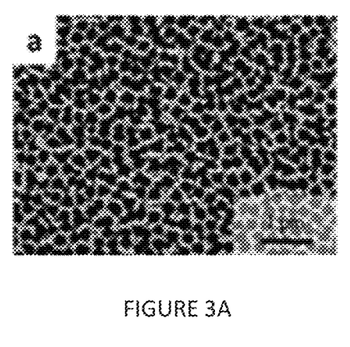
FIGS. 3A-3D are pristine AAO membrane, wood, sponge, and fiber, respectively.
Figure 3B:
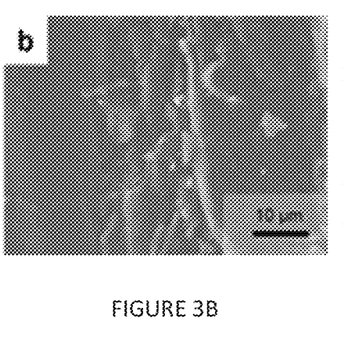
Figure 3C:
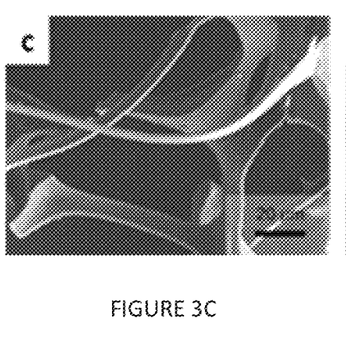
Figure 3D:
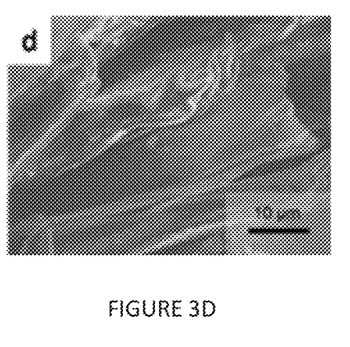
Figure 3E:
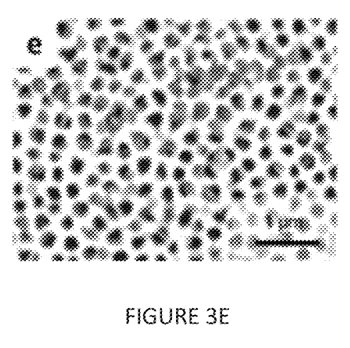
Figure 3F:
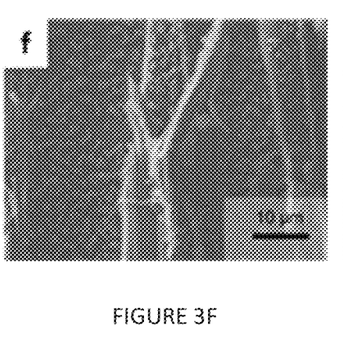
Figure 3G:
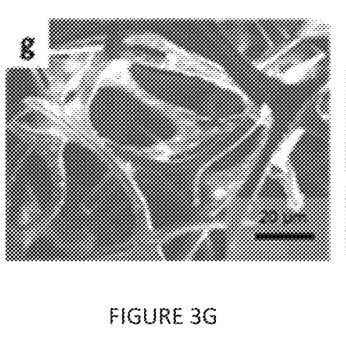
Figure 3H:
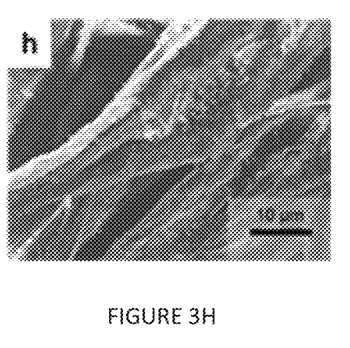
Figure 4A:
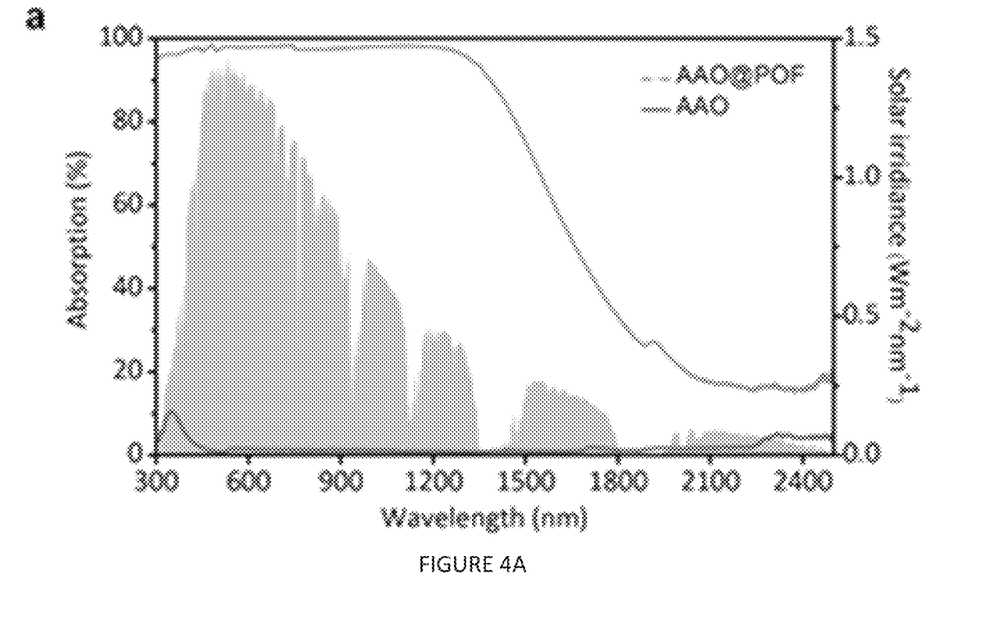
FIG. 4A shows UV-vis/near-infrared ("NIR") spectra of pristine AAO membrane and POF-based AAO membrane, with the AM1.5 standard sunlight spectrum overlaid in gray for comparison.
Figure 4B:
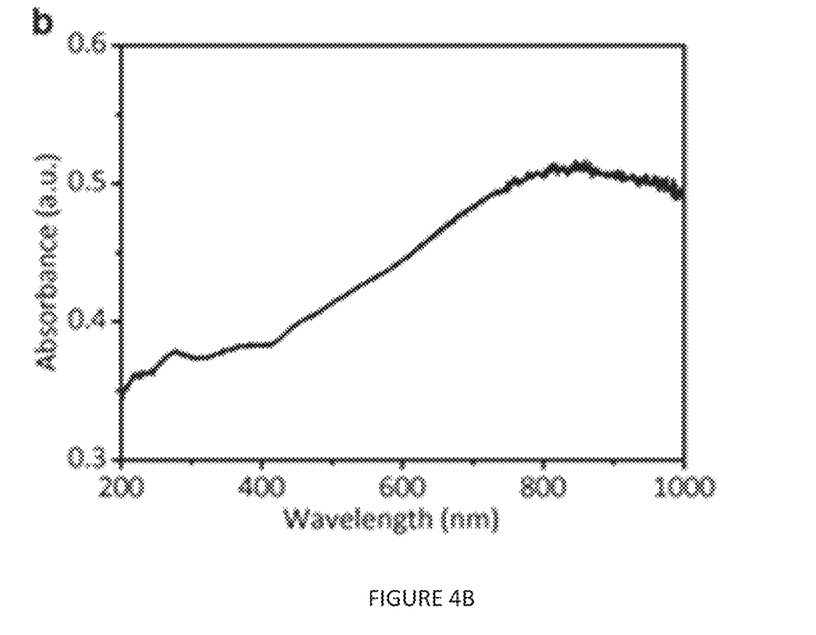
FIG. 4B shows UV-vis spectrum of POF particle solution.
Figure 9:
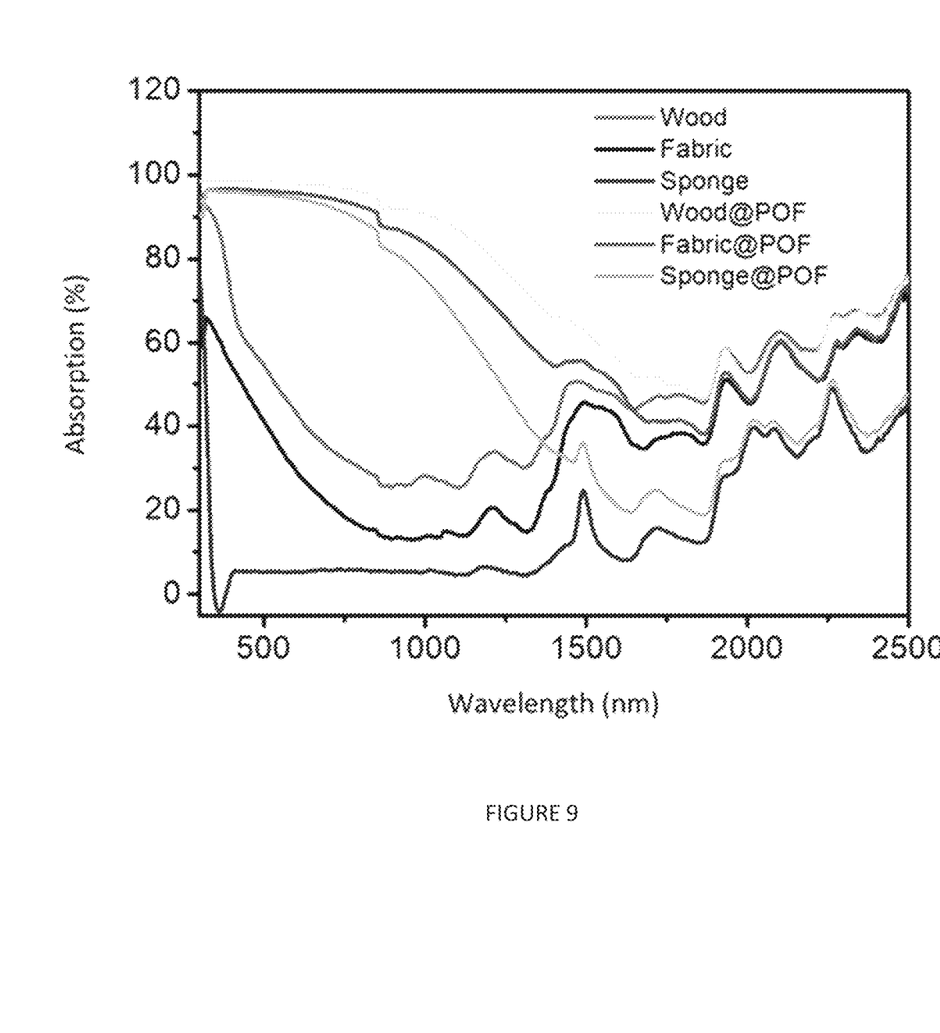
FIG. 9 is a graph of percent absorption for light by wavelength for a series of different substrates, including bare substrates and coated substrates.

The UV-vis spectrum of POF particle solution (FIG. 4B) shows increasing absorption from the UV region to visible region. Time-dependent plane wave ("PW") density functional theory ("DFT") calculations (FIG. 8) of POF light absorption also display broad harvesting across the visible and NIR range. The optical properties of templates@POF were also investigated using a UV-vis/NIR spectrometer (FIG. 4A). In the case of AAO, the nascent material displays little absorption over the entire range of wavelengths, as expected from the visible white appearance (FIG. 2B). Coating with POF particles, however, induces a dramatic change in the light absorption. The UV-vis spectrum of the POF-coated AAO shows low total reflectance, and the measured transmission is negligible. As a result, the light absorbance of the POF membrane is above 95% over the wavelength range of 300-1300 nm, which captures the vast majority of the spectrum of sunlight irradiation. As seen in the limited experimental data in FIG. 9, absorption varies based on the wavelength of light as well as the underlying material.

Figure 5A:
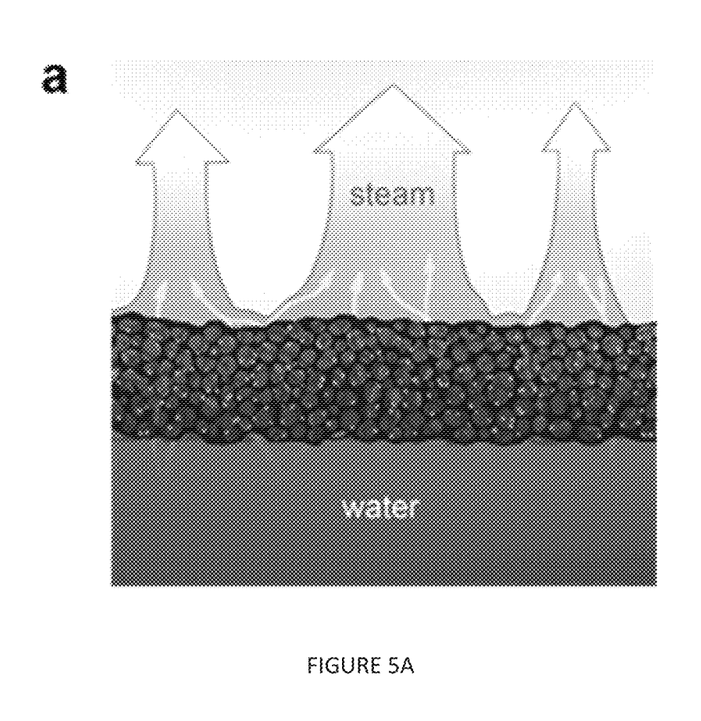
FIG. 5A is a scheme of water evaporation through the POF-based materials.
Figure 5B:
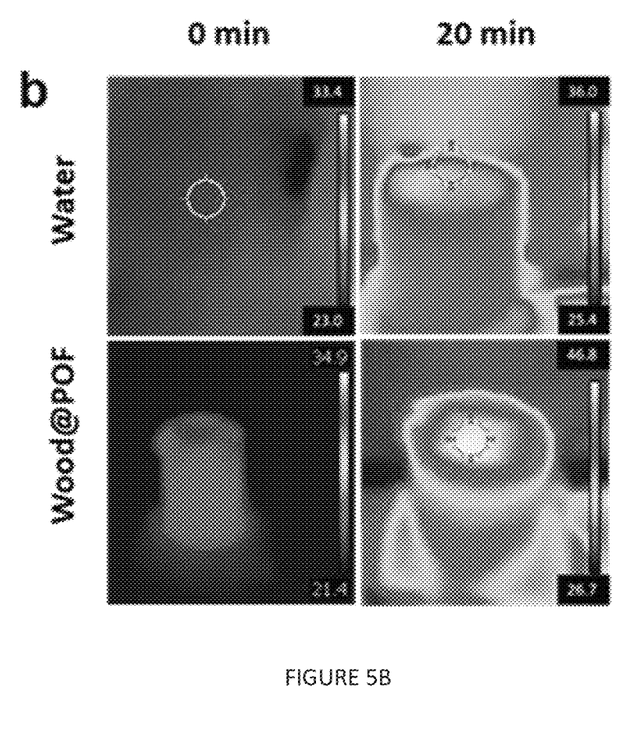
FIG. 5B is a set of infrared images of beakers of water with and without POF-based wood before and after simulated sunlight irradiation.
Figure 5C:
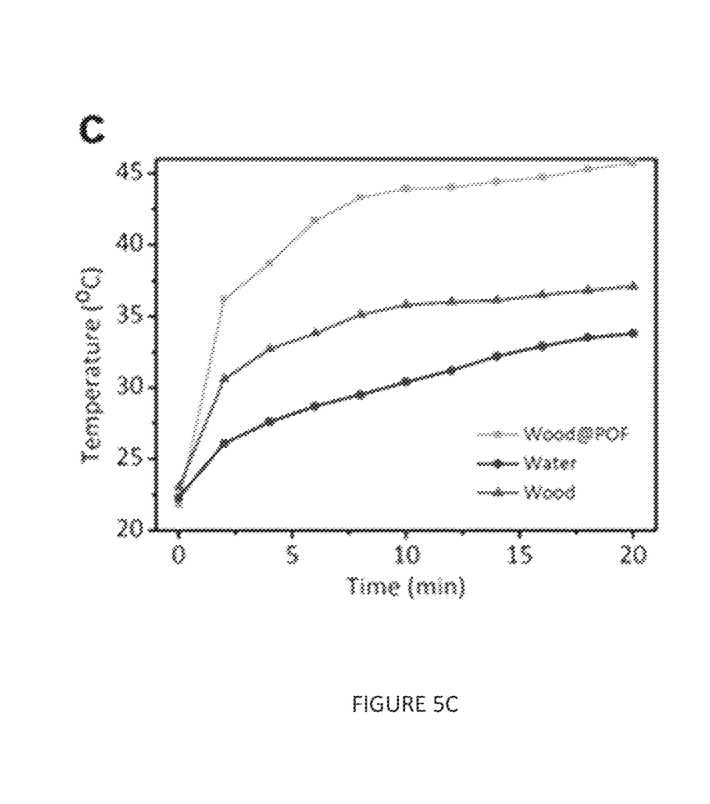
FIG. 5C is a graph of temperature change of beakers with only water, floating wood on water, and POF-based wood on water.
Figure 5D:
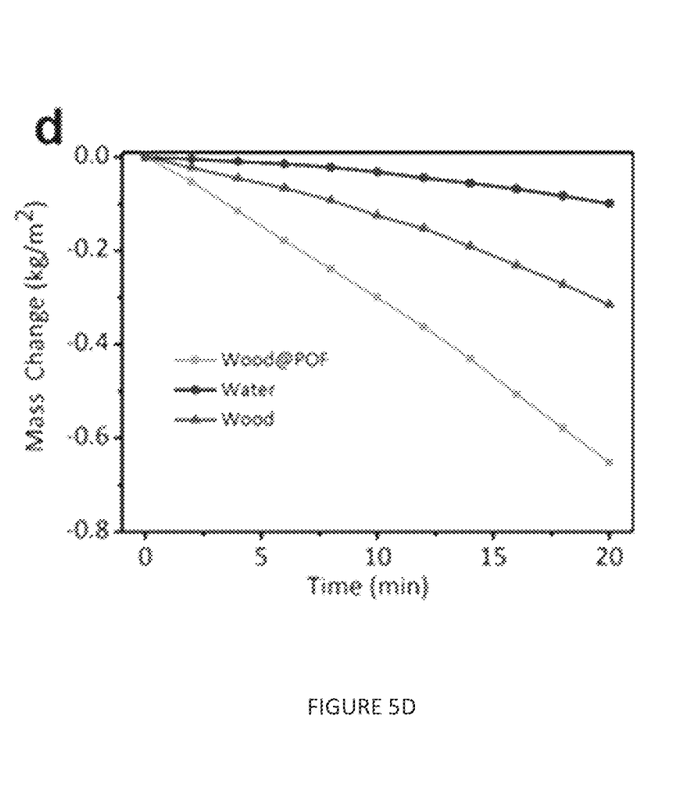
FIG. 5D is a graph of mass change of beakers with only water, floating wood on water, and POF-based wood on water.

To demonstrate the evaporation performance, POF-based absorbers were floated on water and placed under simulated sunlight illumination. In this work, the optical concentration ("$C_{opt}$") is 1.3. FIG. 5A schematically illustrates the mode of operation of such a solar steam generator. When light from the solar simulator illuminates the surface of the POF-based material, the optical energy is converted into heat, which is transferred to the water within the material's pores, thereby accelerating evaporation. As low density, good absorption, porous structure, and low thermal conductivity lay a solid foundation for efficient solar steam generation, the evaporation performance of wood@POF is noted. As shown by infrared imaging in FIG. 5B, the heat was localized on the surface (water-air interface) of the template@POF material. The surface temperature of wood@POF raised quickly with illumination, reaching 45° C. in 20 minutes, while bulk water will only achieve 33° C. in a comparable time period (FIG. 5C). This temperature rise is non-linear. In the initial two minutes, the surface temperature of wood@POF increased from 21.8° C. to 36.8° C., corresponding to a change rate more than three times that of bulk water (22.3° C. to 26.5° C.).

The evaporation tests were performed under simulated sunlight illumination (1.3 Suns intensity in this work). The evaporation rate of wood@POF is 1.95 kg m$^{-2}$ h$^{-1}$. As a comparison, the evaporation of pure water and uncoated wood under the same condition are also recorded, 0.30 kg m$^{-2}$ h$^{-1}$ and 0.94 kg m$^{-2}$ h$^{-1}$, respectively. Clearly, the evaporation efficiency of wood@POF is far surpasses that of both pure water and bare wood, as expected from the enhanced light harvesting. The steam generation efficiency can be calculated by the following equation:

$$\eta = \dot{m} h_{LV}/C_{opt} P_0$$

where $\dot{m}$ refers to the mass change rate, $h_{LV}$ to the liquid-vapor phase change enthalpy, $C_{opt}$ to the optical concentration, and $P_0$ the nominal solar irradiation value of 1 kW m$^{-2}$. Thus, the calculated evaporation efficiency is 84.6% for wood@POF. This high performance is not only attributed to POF structure itself but also this in situ growth method, which preserves the nature of hierarchical cellulose-based structure and low thermal conductivity.

In summary, the above demonstrates a universal, simple, and scalable interface engineering strategy for the fabrication of a solar steam generators based on POF growth. POFs can uniformly in situ grow on the surface of diverse materials with a range of different porosities and hydrophilicities. Wood@POF, using wood as the template, shows 84% overall efficiency toward steam generation under 1.3 Sun illumination. This high performance is attributed to both the superior qualities of wood materials as a scaffold material and the exceptional solar absorptivity of POF particles. This method was also demonstrated with other templates, like sponge@POF, fabric@POF, and membrane@POF. They are all promising candidates as solar steam generators, with the selection of material for a specific application guided by availability, cost, and other factors. POF-based interface engineering design provides a pathway for the scalable fabrication of solar steam generators, with potential ramifications for desalination, wastewater treatment, and beyond.

Definitions

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, and about 1000 would include 900 to 1100.

It should be noted that the term "exemplary," as used herein to describe various embodiments, is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter described herein. Other substitutions, modifications, changes, and omissions may also be made in the design, operating conditions, and arrangement of the various exemplary embodiments without departing from the scope of the present invention.

While this specification contains many specific implementation details, these should not be construed as limitations on the scope of any inventions or of what may be claimed but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method of fabricating a photothermal material comprising:
   providing, in an acidic solution, a porous support scaffold having pores of at least 10 nm average diameter to a reaction vessel;
   adding a pyrrole to the reaction vessel; and
   reacting the pyrrole with a terepthalaldehyde, added to the reaction vessel after providing of the porous support scaffold, by acid-catalyzed dehydration forming a plurality of porphyrin-based covalent organic frameworks particles on the porous support scaffold, the plurality of porphyrin-based covalent organic frameworks particles cover 20-50% of a surface of the porous support scaffold.

2. The method of claim 1, wherein the pyrrole and the terepthalaldehyde are mixed in a 1:1 ratio for reacting.

3. The method of claim 2, further comprising adding terepthalaldehyde acid as a catalyzer.

4. The method of claim 2, wherein the pyrrole is present in a nitrobenzene solvent prior to mixing with the terepthalaldehyde.

5. The method of claim 1, wherein the reacting is at temperature of 50-150° C.

6. The method of claim 1, wherein reacting is for a period of 3-72 hours.

7. The method of claim 6, wherein the period is for 6-12 hours.

8. The method of claim 1, further comprising washing the particles and support scaffold.

9. The method of claim 1, further comprising, after reacting, drying the plurality of porphyrin-based covalent organic frameworks particles on the support scaffold 50-150° C. for 1-4 hours.

10. The method of claim 1, wherein the terepthalaldehyde comprises benzene-1,4, dialdehyde (BDA).

11. The method of claim 1, wherein the porous support scaffold comprises a material selected from the group consisting of wood, AAO membrane, sponge, cork, ceramic, and fabric.

* * * * *